United States Patent
Chen

(10) Patent No.: US 11,273,241 B2
(45) Date of Patent: Mar. 15, 2022

(54) BREAST FLANGE FOR DIRECT COUPLING TO BREAST PUMP FITTING

(71) Applicant: LacTeck LLC, Watertown, MA (US)

(72) Inventor: Juan Chen, Watertown, MA (US)

(73) Assignee: LacTeck LLC, Watertown, MA (US)

( * ) Notice: Subject to any disclaimer, the term of this patent is extended or adjusted under 35 U.S.C. 154(b) by 197 days.

(21) Appl. No.: 16/162,131

(22) Filed: Oct. 16, 2018

(65) Prior Publication Data

US 2019/0209750 A1    Jul. 11, 2019

Related U.S. Application Data

(60) Provisional application No. 62/636,280, filed on Feb. 28, 2018, provisional application No. 62/616,012, filed on Jan. 11, 2018.

(51) Int. Cl.
| | | |
|---|---|---|
| *A61M 1/06* | (2006.01) | |
| *A61J 13/00* | (2006.01) | |
| *A61M 1/00* | (2006.01) | |

(52) U.S. Cl.
CPC .............. *A61M 1/064* (2014.02); *A61J 13/00* (2013.01); *A61M 1/74* (2021.05); *A61M 2209/088* (2013.01); *A61M 2210/1007* (2013.01)

(58) Field of Classification Search
CPC ........ A61M 1/064; A61M 1/06; A61M 1/062; A61M 1/066; A61M 1/068; A61M 1/0031; A61M 2209/088; A61M 2210/1007; A61J 13/00
See application file for complete search history.

(56) References Cited

U.S. PATENT DOCUMENTS

| | | | |
|---|---|---|---|
| 5,049,126 A | 9/1991 | Larsson | |
| 5,885,246 A | 3/1999 | Ford | |
| 6,387,072 B1 * | 5/2002 | Larsson | A61M 1/064 604/74 |
| 6,887,217 B1 * | 5/2005 | Logan | A41C 3/04 604/74 |
| 2004/0087898 A1 * | 5/2004 | Weniger | A61M 1/064 604/74 |
| 2005/0154348 A1 * | 7/2005 | Lantz | A61M 1/06 604/74 |
| 2005/0154349 A1 * | 7/2005 | Renz | A61M 1/82 604/74 |

(Continued)

OTHER PUBLICATIONS

Senia Waldberg, "The Ultimate Breast Pump—Annabella," https://www.indiegogo.com/projects/the-ultimate-breast-pump-annabella#/, Nov. 4, 2017.

*Primary Examiner* — Theodore J Stigell
*Assistant Examiner* — Rachel T. Smith
(74) *Attorney, Agent, or Firm* — Sunstein LLP

(57) ABSTRACT

A breast flange has a cup portion shaped to receive a lactating female breast, a funnel portion coupled to the cup portion and shaped to receive areola and nipple regions of the lactating female breast and to be in contact with the areola region, and a neck portion coupled to the funnel portion and configured to be coupled directly to a breast pump fitting. At least the funnel portion is made of a pliable and resilient material, the material having a thickness. The funnel portion has a set of windows, each window defined by a reduction in thickness of the material and configured to deflect in the presence of suction so as to mimic action of a tongue of a nursing baby.

8 Claims, 7 Drawing Sheets

(56) References Cited

U.S. PATENT DOCUMENTS

| | | | |
|---|---|---|---|
| 2005/0245860 A1* | 11/2005 | Britto | A61M 1/066 604/74 |
| 2014/0052057 A1* | 2/2014 | Darnell | A61M 1/82 604/74 |
| 2016/0058928 A1* | 3/2016 | Nowroozi | A61M 1/066 604/74 |
| 2018/0078687 A1* | 3/2018 | Alvarez | A61M 1/06 |

* cited by examiner

BREAST FLANGE FOR DIRECT COUPLING TO BREAST PUMP FITTING

RELATED APPLICATIONS

The present application claims priority to U.S. Application No. 62/616,012, entitled "Nipple and Areola Massaging Flange" and filed Jan. 11, 2018, which is hereby incorporated by reference in its entirety. The present application also claims priority to U.S. Application No. 62/636,280, entitled "Nipple and Areola Massaging and Compressing Flange" and filed Feb. 28, 2018, which is hereby incorporated by reference in its entirety.

TECHNICAL FIELD

The present invention relates to breast flanges and methods for direct coupling to a breast pump fitting and pumping breast milk, and more particularly to breast flanges configured to stimulate the areola and nipple regions so as to mimic action on the breast of a tongue of a nursing baby.

BACKGROUND ART

Existing breast pumping accessories that massage lactating female breasts to aid the pumping of breast milk suffer from numerous deficiencies. A conventional massage unit can be inserted into a rigid breast flange, which is then coupled to a breast pump. Because inserting the massage unit into the rigid breast flange reduces its inner diameter, the resulting rubbing between the areola and nipple regions of the breast against the wall of the massage unit may cause the lactating mother discomfort or pain. Moreover, since both the massage unit and the rigid breast flange must be washed after each use, such breast pumping accessories require higher degrees of maintenance. Additionally, the combination of massage unit and rigid breast flange may be prone to malfunctioning because use of the combination depends on the presence of an effective seal between the two components, to apply adequate suction to the breast.

SUMMARY OF THE EMBODIMENTS

In some embodiments, the breast flange of the present invention is configured to assist in milk extraction during breast pumping. The embodiments provide compression to the breast, including its areola and nipple regions, to encourage milk expression as the breast flange replicates the action on the breast of a tongue of a nursing baby.

In one embodiment, the invention provides a breast flange comprising a cup portion shaped to receive the breast, a funnel portion coupled to the cup portion, the funnel portion having an interior surface shaped to receive an areola region and a nipple region of the breast and to be in contact with the areola region, and a neck portion coupled to the funnel portion and configured to be coupled directly to a breast pump fitting, so that suction pulses from the breast pump are conveyed via the neck portion, the funnel portion, and the cup portion to the breast. At least the funnel portion is made of a pliable and resilient material, which has a thickness. The funnel portion has a set of windows, and each window is defined by a reduction in thickness of the material, relative to the rest of the funnel portion. Each window is configured to deflect in the presence of suction. The suction pulses produce corresponding deflections of each window so as to mimic action on the breast of a tongue of a nursing baby.

In some embodiments, the cup portion, the funnel portion, and the neck portion are integrally formed from a single piece of material that is pliable and resilient. Exemplary materials include silicone, natural rubber, and nitrile.

In some embodiments, the cup portion, the funnel portion, and the neck portion are formed from different types of pliable and resilient material and/or different types of rigid material. For example, the cup portion and the neck portion can be made of polypropylene plastic and the funnel portion can be made of silicone, natural rubber, or nitrile.

In some embodiments, the funnel portion has a single window defined by a reduction in thickness of the material, relative to the rest of the funnel portion and the window is configured to deflect in the presence of suction, and the suction pulses produce corresponding deflections of the window so as to mimic action on the breast of a tongue of a nursing baby.

In various embodiments, the breast flange further comprises a set of ridges formed in the interior surface of the funnel portion in the set of windows, the set of ridges configured to provide additional stimulation to the areola region and the nipple region.

In some embodiments, a vertical section of each ridge is generally semicircular.

In some embodiments, each ridge is half oval.

In some embodiments, at least one ridge is a different shape from at least one other ridge.

Advantages of embodiments of the invention include improved stimulation of lactating breasts by mimicking action on the breast of a tongue of a nursing baby, simplification of finding the right size of breast flange, and time savings in cleaning. In various embodiments, the invention provides a more comfortable alternative flange for lactating women who have experienced pain while pumping breast milk using conventional rigid breast flanges. The increased efficiency of these embodiments can reduce the amount of time a lactating woman must devote to pumping, and the stimulation provided by the solution can increase milk production. No existing breast flanges are designed to mimic the tongue movements of a nursing baby, which are effective at stimulating a lactating woman's areola region and nipple region, in the manner performed by embodiments of the invention. Without a standard of measurement, lactating women cannot easily identify their correct size of breast flange, and a breast flange made of a pliable and resilient material allows a single size to accommodate a wider variation in breast sizes. For mimicking action on the breast of a tongue of a nursing baby, the funnel portion of the breast flange has a set of windows, and each window is defined by a reduction in thickness of the material compared to the rest of the funnel portion. Additionally, each window is configured to deflect in the presence of suction, and the suction pulses produce corresponding deflections of each window so as to mimic action on the breast of a tongue of a nursing baby. Since the pliable and resilient material embodiments of the invention reduce abrasion to the breast, these embodiments can provide a comfortable alternative to rigid breast flanges. Stimulating the areola region and nipple region encourage natural let-down reflexes and therefore increase the efficiency of milk extraction and improve milk production.

As breast flange embodiments of the present invention can replace the conventional combination of massaging unit and rigid breast flange, a lactating woman can simply wash one part, instead of two.

A further advantage of embodiments of the present invention is that they are designed to be used with commercially available vacuum breast pumps. A user of an embodiment of a breast flange in accordance with the present invention may use it as an accessory with a typical breast pump; this is particularly advantageous for a woman who encounters lactation problems after purchasing a breast pump, as she can use the embodiment with her already-purchased pump.

Details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

The foregoing features of embodiments will be more readily understood by reference to the following detailed description, taken with reference to the accompanying drawings, in which.

Like reference symbols in the various drawings indicate like elements.

DETAILED DESCRIPTION OF SPECIFIC EMBODIMENTS

Definitions. As used in this description and the accompanying claims, the following terms shall have the meanings indicated, unless the context otherwise requires:

A breast pump "fitting" is component of the breast pump, for removable attachment to a breast flange, which conveys suction from the breast pump to the breast flange.

A "set" has at least one member.

Conventional breast pumping accessories use a rigid breast flange and apply only a negative pressure to the areola and nipple regions of a breast. Consequently, the rigid breast flange fails to directly stimulate nerve endings in the areola and nipple regions. Although conventional massage units may be placed inside the rigid breast flanges to provide such stimulation, using an additional component with the rigid breast flange incurs risks of misfit and breaking the seal between the breast and the breast pump, and also requires more cleaning. Embodiments of the present invention overcome these difficulties.

Figure 1:
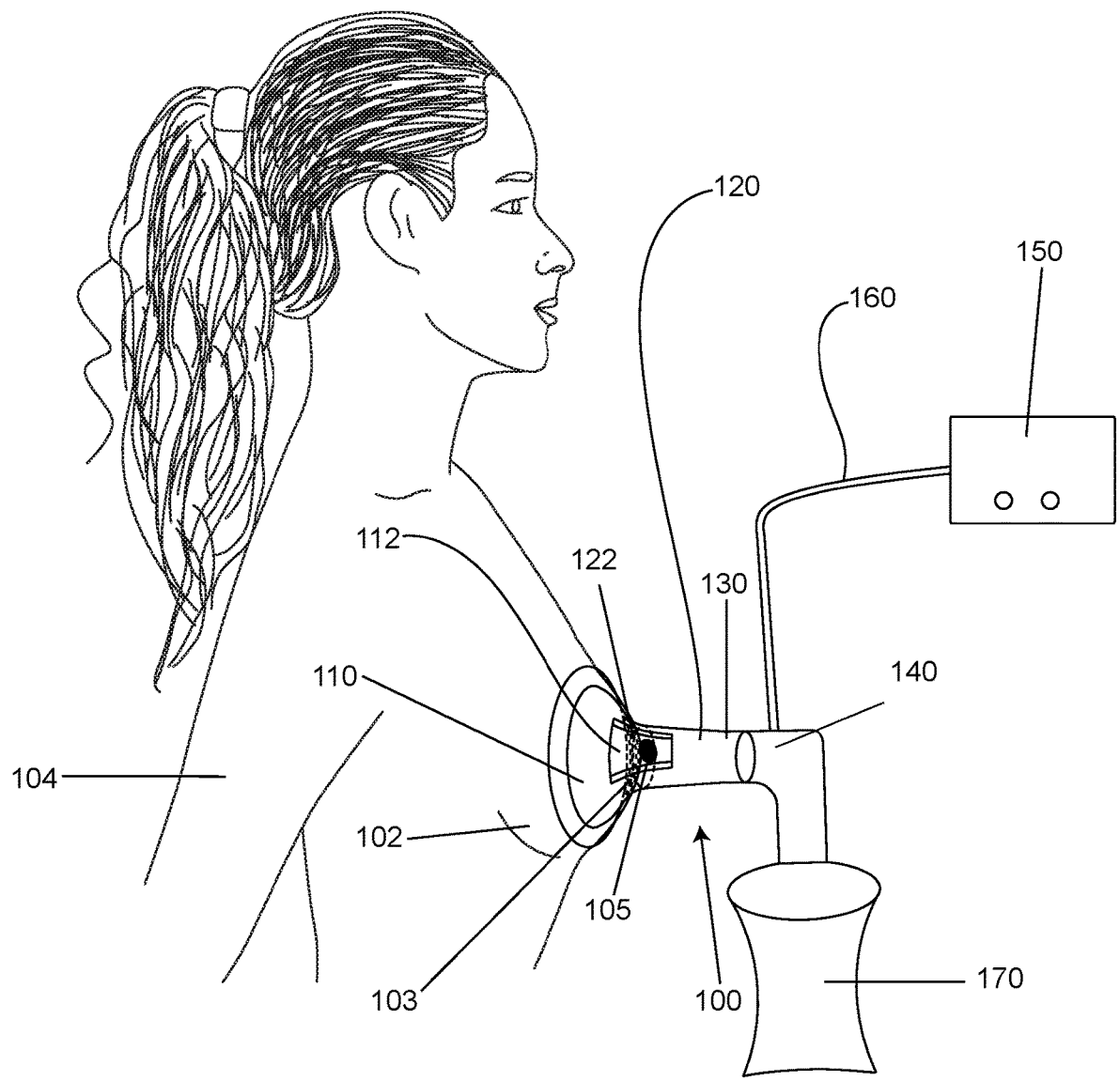
FIG. 1 is a simplified side view of a user employing a breast flange, in accordance with an embodiment of the present invention, which includes a single window to mimic a tongue of a nursing baby, with a commercial vacuum breast pump.

FIG. 1 is a simplified side view of a user employing a breast flange 100, in accordance with an embodiment of the present invention, which includes a single window 112 to mimic a tongue of a nursing baby, with a commercial vacuum breast pump 150. The breast flange 100 is being used to aid milk extraction from a breast 102 of a lactating woman 104. A cup portion 110 of the breast flange 100 is placed on the breast 102 so that an interior surface 122 of a funnel portion 120 of the breast flange 100 receives an areola region 103 and a nipple region 105 of the breast 102. The funnel portion 120 contacts the areola region 103, and also encloses the nipple region 105. A neck portion 130 of the breast flange 100 is removably coupled with a breast pump fitting 140, which is connected to a breast pump 150 via a breast pump tubing 160, although, in other embodiments, the breast flange 100 and the breast pump fitting 140 are an integral unit that is configured to be directly connected to the breast pump tubing 160. The breast pump fitting 140 is coupled to a milk collection bottle 170. When the breast pump 150 is turned on, suction pulses are conveyed through the breast pump fitting 140 and the breast flange 100 to the breast 102. The suction pulses cause the nipple region 105 of the breast 102 to move synchronously back and forth within the funnel portion 120 and the neck portion 130 of the breast flange 100. The suction pulses also cause a set of single unique windows 112 on the funnel portion 120 of the breast flange 100 to deflect and compress the areola region 103 and nipple region 105, in a manner similar to the action on the breast 102 of a tongue of a nursing baby. The combination of compression and suction that the breast flange 100 applies to the breast 102 (also referred to herein as "massaging") encourages a natural let-down reflex so that the breast 102 releases milk, and also stimulates the breast 102 to increase its production of milk.

Figure 2:
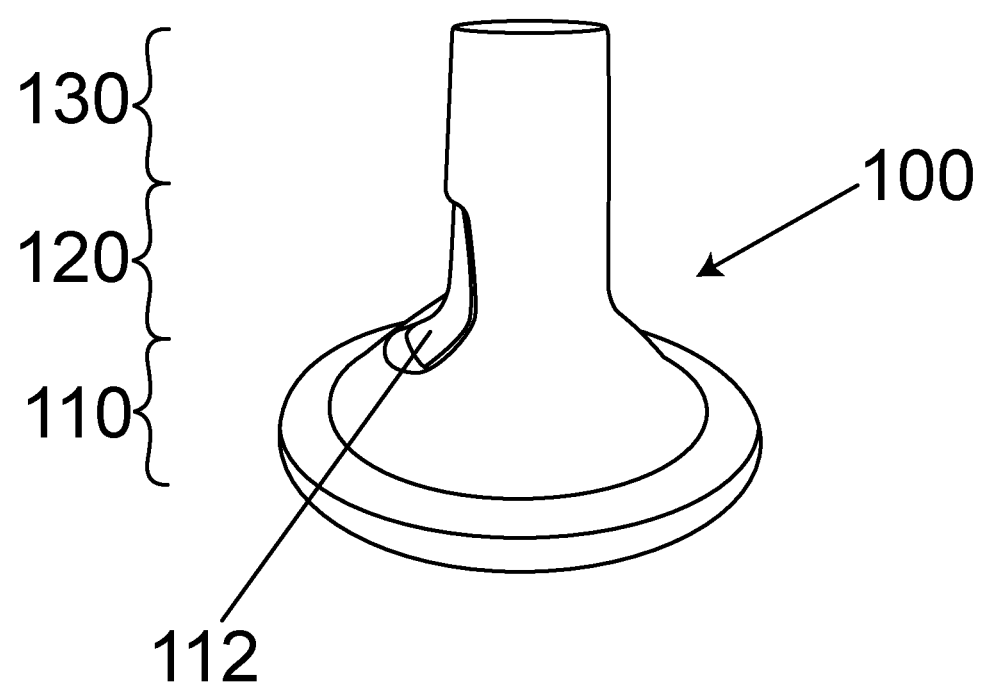
FIG. 2 shows a perspective view of the breast flange of FIG. 1.

Now referring to FIG. 2, which shows a perspective view of the breast flange 100 of FIG. 1, the breast flange 100 includes the cup portion 110, the funnel portion 120, and the neck portion 130. The cup portion 110, the funnel portion 120, and the neck portion 130 are integrally formed from a single piece of pliable and resilient material, such as silicone. The funnel portion 120 contains a window 112 defined by an area of the material having a thickness is reduced, compared to the thickness of material in the rest of the funnel portion 120. The window 112 deflects in the presence of suction. The size and shape of window 112 are generally similar to those of a baby's tongue. In some embodiments, the window 112 has an area between 100 and 2,500 $mm^2$ and a generally trapezoid shape, a circular shape, or an oval shape. The height of the breast flange 100 can be between 10-120 mm. The inside diameter of the cup portion 110 can be between 10-100 mm. The inside diameter of the funnel portion 120 can be between 10-40 mm, and the inside diameter of the neck portion 130 can be between 20-50 mm. In some embodiments, the breast flange 100 is made of silicone with Shore durometer of 50 A. In these embodiments, the cup portion 110, the funnel portion 120, and the neck portion 130 exhibit the same thickness. This thickness can be between 4-7 mm, and the thickness of the window 112 can be between 0.5-3.0 mm. In further embodiments, the breast flange 100 is made of silicone with a Shore durometer of 60 A. In these embodiments, the material thickness of the cup portion 110, the funnel portion 120, and the neck portion 130 can be between 3-6 mm, and the window 112 can be between 0.5-2.5 mm. In additional embodiments, the breast flange 100 is made of silicone with a Shore durometer of 70 A. The cup portion 110, the funnel portion 120, and the neck portion 130 can be between 2-5 mm, and the thickness of the window 112 can be between 0.5-2.0 mm.

Figure 3:
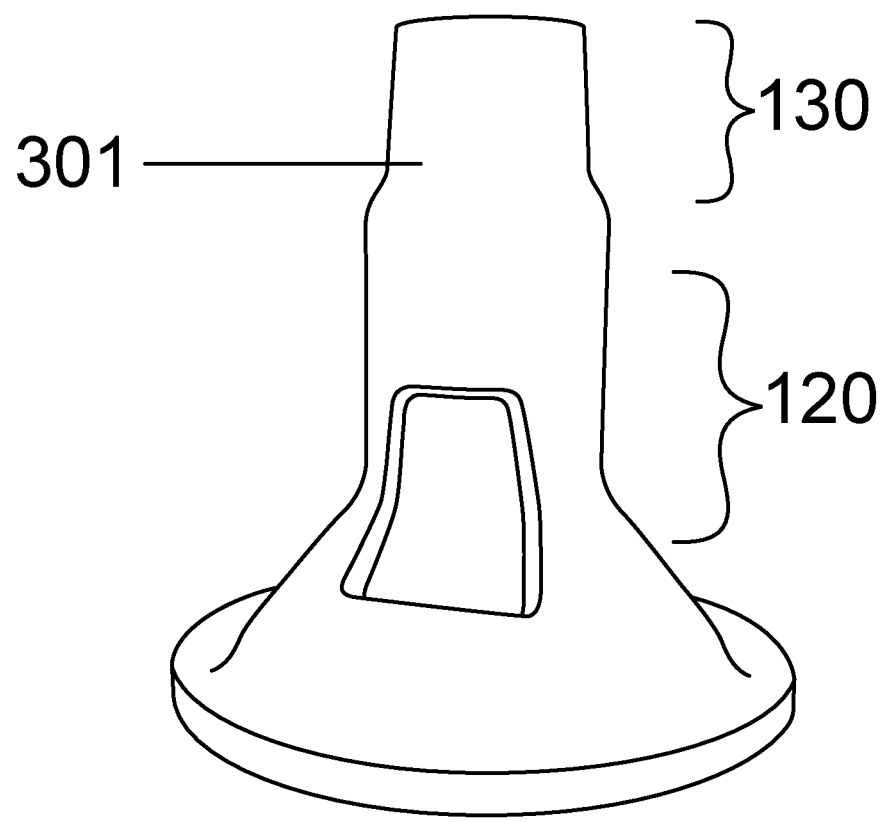
FIG. 3 shows a perspective view of a breast flange, in accordance with another embodiment of the present invention, which includes a single window to mimic a tongue of a nursing baby, and a reduced diameter neck portion.

FIG. 3 shows a perspective view of a breast flange 100, in accordance with another embodiment of the present invention, which includes a single window 112 to mimic a tongue of a nursing baby, and a reduced diameter neck portion 301. The neck portion 301 must be sized, at the end distal from the cup portion 110, so as to be coupled to a breast pump fitting 140. However, the sizing of the funnel portion 120 proximate to the cup portion 110 is determined by anatomical requirements of the user. The reduced diameter neck portion 301 is useful to accommodate a funnel portion 120 having a minimum diameter that is relatively larger than that of the neck portion 301.

Figure 4:
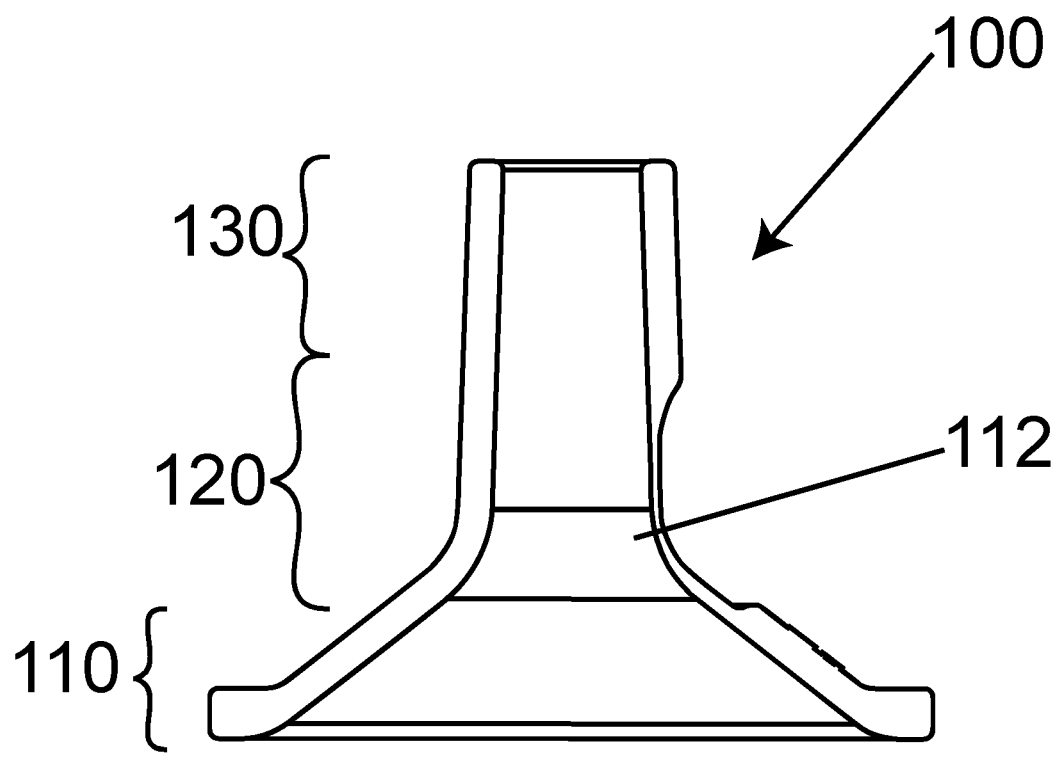
FIG. 4 shows a vertical section view of the breast flange of FIG. 1.

FIG. 4 shows a vertical section view of the breast flange 100 of FIG. 1. The cup portion 110, the funnel portion 120, and the neck portion 130 are integrally formed from a single piece of pliable and resilient material, such as silicone, and the thickness of the breast flange 100 can vary from one portion of the flange 100 to another. In some embodiments, the thickness of any of the cup portion 110, the funnel portion 120, and the neck portion 130 can be between 0.1-10 mm. The thickness of the window 112 can be between 0.1-5 mm, and the thickness can vary from one end of the window 112 to the opposite end. The thickness of the cup portion 110 and the reduced diameter neck portion 301 can be between 1-7 mm. In some embodiments, the thickness of the window 112 is 10-80% that of the thickness of the cup portion 110 or the neck portion 130, and the surface area of the window 112 is 10-80% that of the surface area of the funnel portion 120. In further embodiments, the thickness of the window 112 is 20-50% that of the thickness of the cup portion 110 or the neck portion 130, and the surface area of the window 112 is 20-50% that of the surface area of the funnel portion 120.

Figure 5:
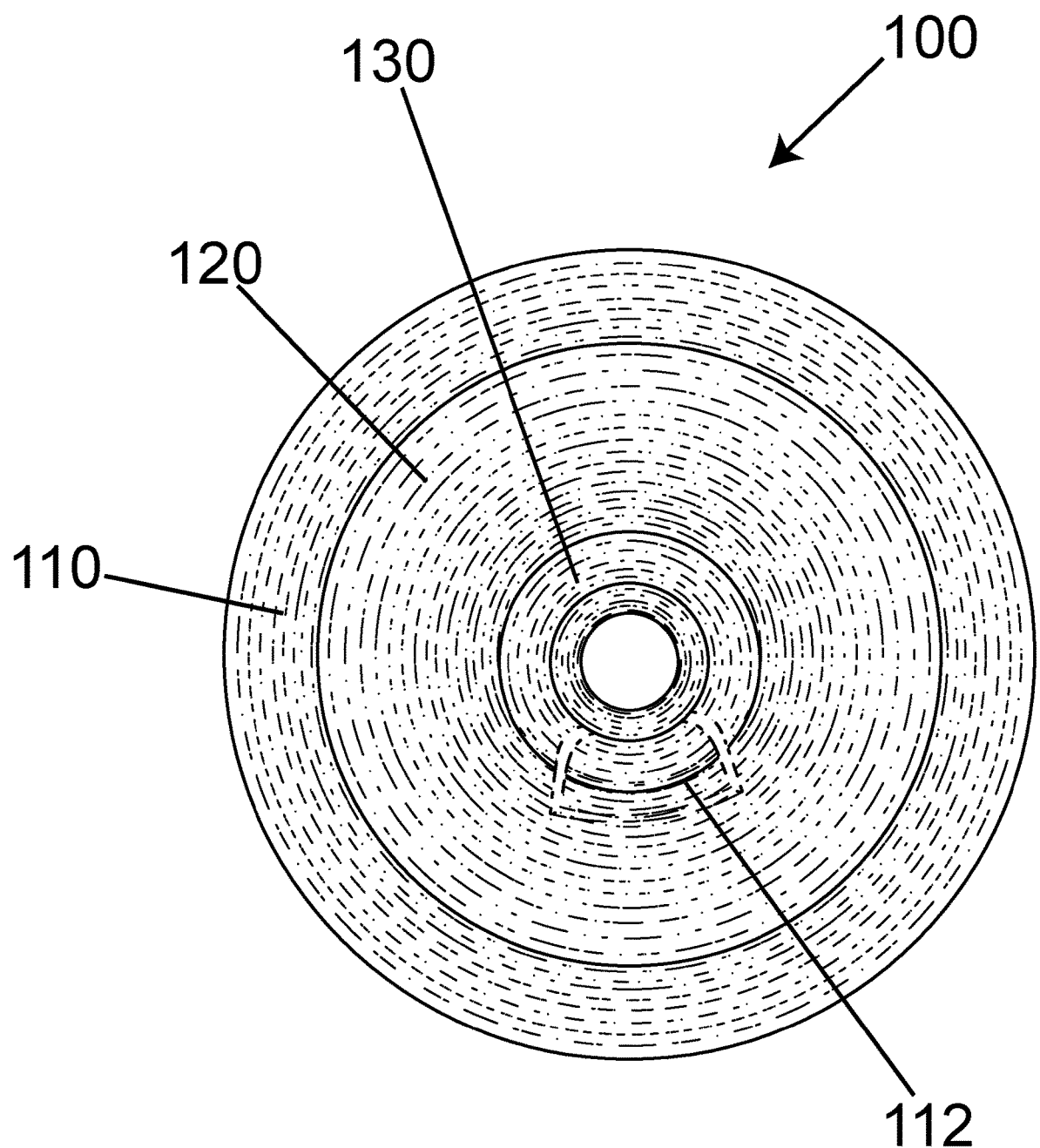
FIG. 5 shows a bottom view of the breast flange of FIG. 1.
Figure 6:
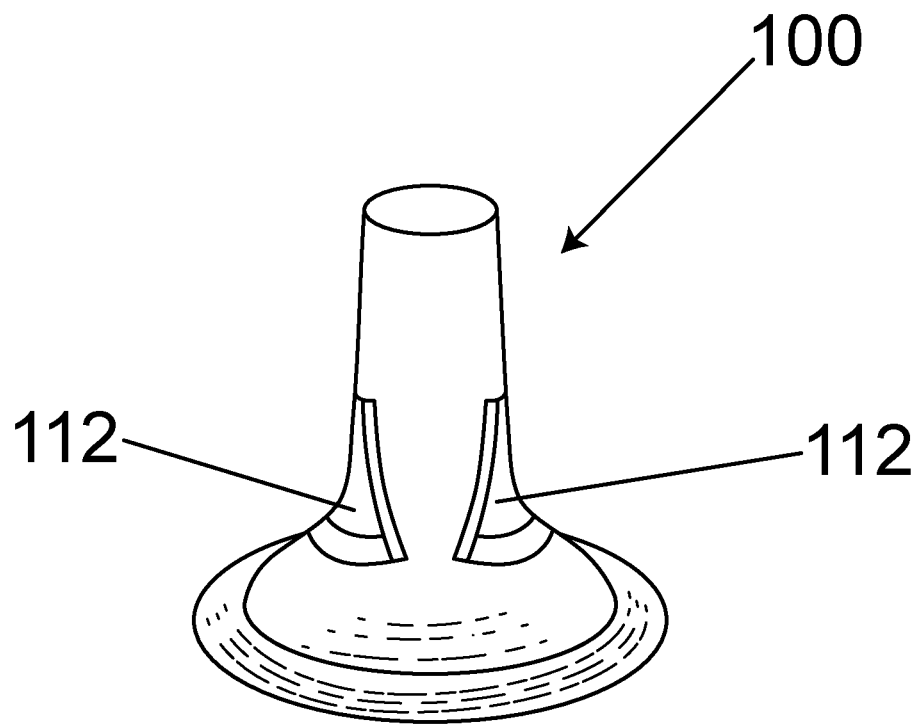
FIG. 6 shows a breast flange with a plurality of windows, wherein each window mimics a tongue of a nursing baby, in accordance with an embodiment of the present invention.

FIG. 5 shows a bottom view of the breast flange 100 of FIG. 1. FIG. 6 shows a breast flange 100 with a plurality of windows 112, wherein each window 112 mimics a tongue of a nursing baby, in accordance with an embodiment of the present invention. Each window 112 is optionally placed equidistantly around the perimeter of the funnel portion 120 of the breast flange 100. Although the embodiment depicted in FIG. 6 shows two windows 112, any other number of windows 112 may be used.

Figure 7:
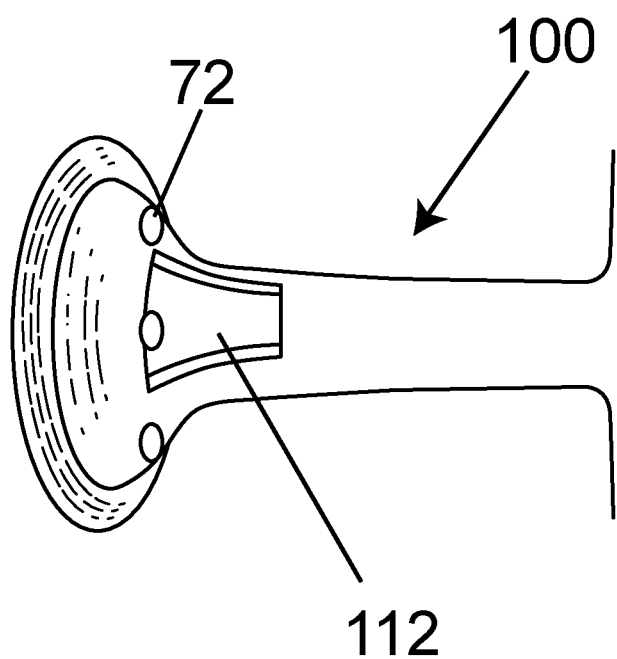
FIG. 7 shows a breast flange with a set of ridges inside the single window that mimics a tongue of a nursing baby, in accordance with an embodiment of the present invention.

FIG. 7 shows a breast flange 100 with a set of ridges 72 inside the single window 112 that mimics a tongue of a nursing baby, in accordance with an embodiment of the present invention. The set of ridges 72 provide additional stimulation during pumping. In some embodiments, a vertical section of each ridge 72 is generally semicircular. In other embodiments, the vertical section of each ridge 72 is half oval. In other embodiments, at least one ridge 72 has a different shape from that of another ridge 72.

In various embodiments, the breast flange 100 is provided in a range of sizes to accommodate different users. For example, the breast flange 100 can be offered in small, medium, and large sizes. The diameter of the cup portion 110, the diameter of a reduced diameter neck portion 301, the size of the window 112, the height of the breast flange 100, and the thicknesses of the different portions of the breast flange 100 can vary from one size to another. The diameter of the cup portion 110 of any of these breast flanges 100 can be between 60-150 mm. The diameter of the reduced diameter neck portion 301 can be between 15-35 mm. The size of the window 112 can be between 100-2500 mm$^2$. The thickness of the different portions of the different sized breast flanges 100 can be between 0.5 mm-10 mm. The breast flange 100 can be of different heights, for example, between 10-120 mm.

In some embodiments, the cup portion 110, the funnel portion 120, the set of windows 112, and the neck portion 130 are made out of different materials. For example, the set of windows 112 can be made of a pliable and resilient material, such as silicone or natural rubber, while the cup portion 110 and the neck portion 130 can be made of non-pliable material, such as polypropylene plastic.

In various embodiments, the neck portion 130 is removable and exchangeable to allow coupling to the fittings of different models of breast pumps. Furthermore, a breast flange 100 may be securely coupled to the breast 102 of a user via a hands-free pumping brassiere (not shown). The user may place a separate breast flange 100 on each of her lactating breasts 102, don a hands-free pumping brassiere to maintain the contact therebetween, and start the pumping of the breast pump.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A breast flange, for conveying suction from a breast pump to a breast of a lactating woman, for extraction of milk from the breast, the breast flange comprising:
   a cup portion shaped to receive the breast;
   a funnel portion coupled to the cup portion, the funnel portion having (i) an exterior surface constituting a part of an exterior surface of the breast flange and (ii) an interior surface shaped to receive an areola region and a nipple region of the breast and to be in contact with the areola region and the nipple region; and
   a neck portion, coupled to the funnel portion and configured to be removably coupled directly to a breast pump fitting, so that suction pulses from the breast pump are conveyed via the neck portion, the funnel portion and the cup portion to the breast;
   wherein the cup portion, the funnel portion, and the neck portion are integrally formed from a single piece of a pliable and resilient material, the material having a thickness, the funnel portion having at least one window, each window (i) having an exterior surface that is coextensive with the exterior surface of the funnel portion, (ii) defined by a reduction in thickness of the material, and (iii) configured to deflect in the presence of each of the suction pulses in a manner wherein presence of each suction pulse causes a corresponding deflection of such window so as to compress a region selected from the group consisting of the areola region, the nipple region, and combinations thereof, so as to mimic action on the breast of a tongue of a nursing baby, wherein the deflection of such window is a single deflection that extends over a substantially entire expanse of such window.

2. A breast flange according to claim 1, wherein the material is silicone.

3. A breast flange according to claim 1, wherein the at least one window has only one member, so that the funnel portion has a single unique window.

4. A breast flange according to claim 3, further comprising a set of ridges formed in the interior surface of the funnel portion in the single unique window.

5. A breast flange according to claim 4, wherein a vertical section of each ridge is generally semicircular.

6. A breast flange according to claim 4, wherein each ridge is half oval.

7. A method for massaging areola and nipple regions to aid breast milk expression and production of a lactating woman, the method comprising:

coupling a breast flange into a breast pump fitting, the breast flange comprising:
  a cup portion shaped to receive the breast;
  a funnel portion coupled to the cup portion, the funnel portion having (i) an exterior surface constituting a part of an exterior surface of the breast flange and (ii) an interior surface shaped to receive an areola region and a nipple region of the breast and to be in contact with the areola region; and
  a neck portion, coupled to the funnel portion and configured to be removably coupled directly to the breast pump fitting, so that suction pulses from a breast pump are conveyed via the neck portion, the funnel portion and the cup portion to the breast;
  wherein the cup portion, the funnel portion, and the neck portion are integrally formed from a single piece of a pliable and resilient material, the material having a thickness, the funnel portion having at least one window, each window (i) having an exterior surface that is coextensive with the exterior surface of the funnel portion, (ii) defined by a reduction in thickness of the material, and (iii) configured to deflect in the presence of each of the suction pulses in a manner wherein presence of each suction pulse causes a corresponding deflection of such window so as to compress a region selected from the group consisting of the areola region, the nipple region, and combinations thereof, so as to mimic action on the breast of a tongue of a nursing baby, wherein the deflection of such window is a single deflection that extends over a substantially entire expanse of such window;
placing at least one breast flange onto a breast of a lactating woman;
securing at least one breast flange with a hands-free pumping brassiere; and
starting pumping of the breast pump.

8. A method for massaging areola and nipple regions to aid breast milk expression and production of a lactating woman, the method comprising:
  coupling a breast flange into a breast pump fitting, the breast flange comprising:
    a cup portion shaped to receive the breast;
  a funnel portion coupled to the cup portion, the funnel portion having (i) an exterior surface constituting a part of an exterior surface of the breast flange and (ii) an interior surface shaped to receive an areola region and a nipple region of the breast and to be in contact with the areola region; and
  a neck portion, coupled to the funnel portion and configured to be removably coupled directly to the breast pump fitting, so that suction pulses from a breast pump are conveyed via the neck portion, the funnel portion and the cup portion to the breast;
    wherein the cup portion, the funnel portion, and the neck portion are integrally formed from a single piece of a pliable and resilient material, the material having a thickness, the funnel portion having at least one window, each window (i) having an exterior surface that is coextensive with the exterior surface of the funnel portion, (ii) defined by a reduction in thickness of the material, and (iii) configured to deflect in the presence of each of the suction pulses in a manner wherein presence of each suction pulse causes a corresponding deflection of such window so as to compress a region selected from the group consisting of the areola region, the nipple region, and combinations thereof, so as to mimic action on the breast of a tongue of a nursing baby, wherein the deflection of such window is a single deflection that extends over a substantially entire expanse of such window
  placing at least one breast flange onto a breast of a lactating woman; and starting pumping of the breast pump.

\* \* \* \* \*